United States Patent
Kusner, Jr. et al.

(10) Patent No.: US 7,909,036 B2
(45) Date of Patent: Mar. 22, 2011

(54) ADJUSTABLE HEAD HOLDER FOR USE WITH CT SCANNER

(75) Inventors: Michael Thomas Kusner, Jr., Perrysburg, OH (US); James A. Bertolina, Portage, MI (US); William C. Van Kampen, Saline, MI (US); Joseph Webster Stayman, Ann Arbor, MI (US); Jonathan Alspaugh, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 0 days.

(21) Appl. No.: 12/020,796

(22) Filed: Jan. 28, 2008

(65) Prior Publication Data

US 2008/0178893 A1    Jul. 31, 2008

Related U.S. Application Data

(60) Provisional application No. 60/897,566, filed on Jan. 26, 2007.

(51) Int. Cl.
  *A61G 15/00*    (2006.01)
(52) U.S. Cl. ............... 128/845; 5/637; 5/640; 378/209; 378/20
(58) Field of Classification Search .............. 5/621, 622, 5/625, 637, 601, 632, 640, 643; 378/209, 378/20; 128/845, 870, 869; 602/5, 32
See application file for complete search history.

(56) References Cited

U.S. PATENT DOCUMENTS

| | | | |
|---|---|---|---|
| 4,616,814 A | 10/1986 | Harwood-Nash et al. | |
| 5,081,665 A | 1/1992 | Kostich | |
| 5,233,713 A * | 8/1993 | Murphy et al. ................... | 5/636 |
| 5,276,927 A * | 1/1994 | Day ................................... | 5/622 |
| 5,566,681 A | 10/1996 | Manwaring et al. | |
| 5,661,859 A * | 9/1997 | Schaefer ........................... | 5/621 |
| 5,916,189 A | 6/1999 | Sullenperger et al. | |
| 6,138,302 A * | 10/2000 | Sashin et al. ...................... | 5/600 |
| 6,199,233 B1 | 3/2001 | Kantrowitz et al. | |
| 6,510,852 B1 | 1/2003 | Shiery et al. | |
| 6,526,609 B2 * | 3/2003 | Wong ................................ | 5/601 |
| 7,298,821 B2 * | 11/2007 | Ein-Gal .......................... | 378/68 |
| 7,736,056 B2 * | 6/2010 | Tybinkowski et al. ........ | 378/209 |

* cited by examiner

*Primary Examiner* — Patricia M Bianco
*Assistant Examiner* — Camtu T Nguyen
(74) *Attorney, Agent, or Firm* — Carlson, Gaskey & Olds, P.C.

(57) ABSTRACT

A head holder made of radiolucent material is attached near an end of a table to support a head of a patient during a CT scan. The head holder includes a base portion that supports the shoulders and upper back of the patient and a head rest that supports a patient's head. The head holder is moveable relative to the table in a direction that is generally parallel to a length of the table. A position of the head rest is adjustable in a vertical direction relative to the base portion. The radiolucent material of the head holder does not affect the quality of a resulting CT scan.

31 Claims, 6 Drawing Sheets

ADJUSTABLE HEAD HOLDER FOR USE WITH CT SCANNER

REFERENCE TO RELATED APPLICATIONS

This application claims priority to U.S. Provisional Patent Application No. 60/897,566 filed Jan. 26, 2007.

BACKGROUND OF THE INVENTION

The present invention relates generally to a head holder for use with a CT scanner, and a position of the head holder is adjustable relative to a table.

A CT scanner takes a plurality of x-ray images of a part of a patient to create a three dimensional CT image. In one example CT scanner, a patient lies on a metal table and positions his head on a head holder that is located in a space between arm sections of a gantry of the CT scanner. The plurality of x-ray images are taken while the gantry rotates about an axis of rotation. A computer generates the three dimensional CT image from the plurality of x-ray images.

The prior art head holder is fixed relative to the table. When the patient is positioned on the table, it is possible that a portion of the metal table could be located in the space, which could affect the resulting three dimensional CT image.

SUMMARY OF THE INVENTION

A head holder is attached near an end of a table to support a head of a patient during a CT scan. The head holder is made of radiolucent material, such as carbon fiber. The head holder includes a base portion that supports the patient's upper back and shoulders and a head rest including a head retaining portion that supports the patient's head. The head holder is moveable relative to the table in a direction that is generally parallel to a length of the table.

The base portion and the head rest both include a flange with a plurality of holes. The holes of the flanges are aligned, and an attachment member is received in the aligned holes to secure the head retaining portion to the base portion. A position of the head rest can be adjusted in a generally vertical direction relative to the base portion by aligning different holes of the flanges.

During a CT scan, the head holder is received in a space defined between arm sections of a gantry of the CT scanner. The radiolucent material of the head holder received in the space does not affect the quality of the resulting CT scan.

These and other features of the present invention will be best understood from the following specification and drawings.

DETAILED DESCRIPTION OF THE PREFERRED EMBODIMENT

Figure 1:
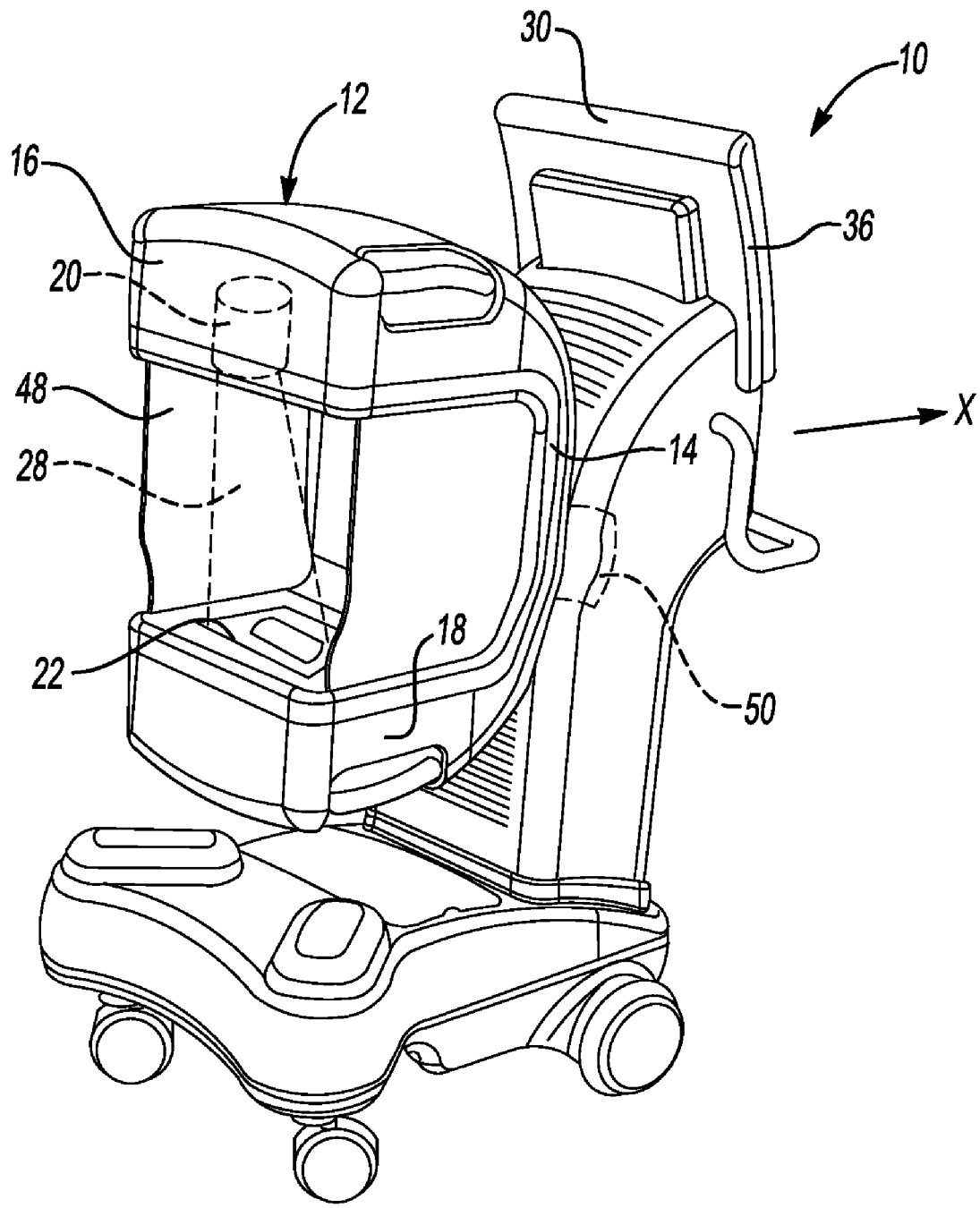
FIG. 1 schematically illustrates a CT scanner.

FIG. 1 illustrates a CT scanner 10 including a gantry 12 that supports and houses components of the CT scanner 10. In one example, the gantry 12 includes a cross-bar section 14, and a first arm 16 and a second arm 18 each extend substantially perpendicularly from opposing ends of the cross-bar section 14 to form the c-shaped gantry 12. The first arm 16 houses an x-ray source 20 that generate x-rays 28. In one example, the x-ray source 20 is a cone-beam x-ray source. The second arm 18 houses a complementary flat-panel detector 22. The x-rays 28 are directed toward the detector 22 which includes a converter (not shown) that converts the x-rays 28 from the x-ray source 20 to visible light and an array of photodetectors behind the converter to create an image. As the gantry 12 rotates about the patient P, the detector 22 takes a plurality of x-ray images at a plurality of rotational positions. Various configurations and types of x-ray sources 20 and detectors 22 can be utilized, and the invention is largely independent of the specific technology used for the CT scanner 10.

Figure 2:
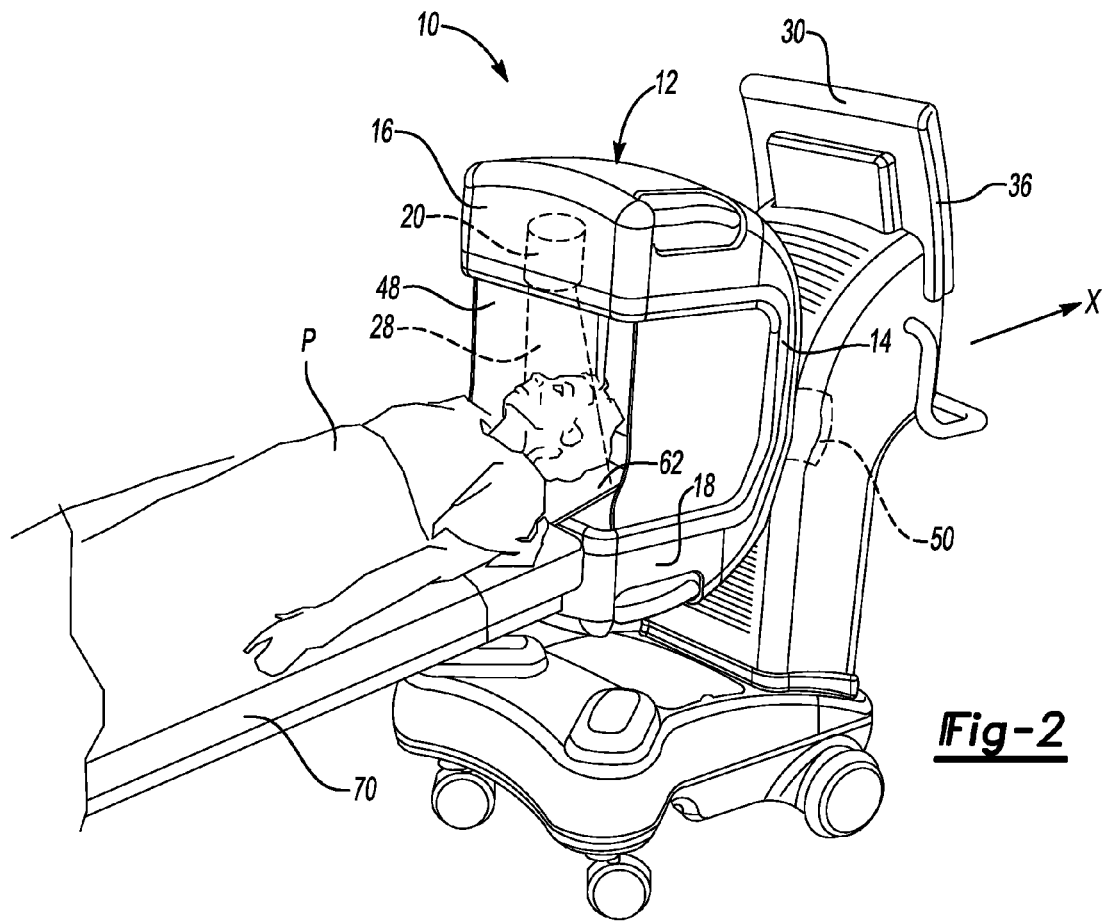
FIG. 2 illustrates the CT scanner with a part of a patient received in the CT scanner.

FIG. 2 illustrates the CT scanner 10 with a part of the patient P received in a space 48 between the first arm 16 and the second arm 18. A motor 50 rotates the gantry 12 about an axis of rotation X to obtain a plurality of x-ray images of the patient P at the plurality of rotational positions. The axis of rotation X is positioned between the x-ray source 20 and the detector 22. The gantry 12 can be rotated approximately slightly more than 360 degrees about the axis of rotation X. In one example, as shown in FIGS. 1 and 2, the axis of rotation X is substantially horizontal. In this example, the patient P is typically lying down on a table 70, and a head H of the patient P rests on a head holder 62 adjustably attached to the table 70.

Figure 3:
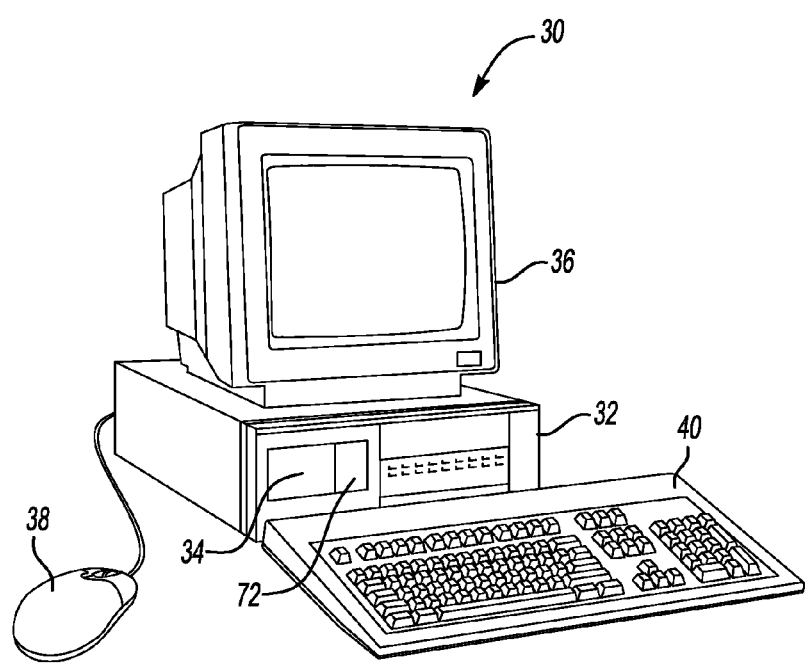
FIG. 3 illustrates a computer employed with the CT scanner.

As shown schematically in FIG. 3, the CT scanner 10 further includes a computer 30 having a microprocessor or CPU 32, a storage 34 (memory, hard drive, optical, and/or magnetic, etc), a display 36, a mouse 38, a keyboard 40 and other hardware and software for performing the functions described herein. The computer 30 powers and controls the x-ray source 20 and the motor 50. The plurality of x-ray images taken by the detector 22 are sent to the computer 30. The computer 30 generates a three-dimensional CT image from the plurality of x-ray images utilizing any known techniques and algorithms. The three-dimensional CT image is stored on the storage 34 of the computer 30 and can be displayed on the display 36 for viewing.

Figure 4:
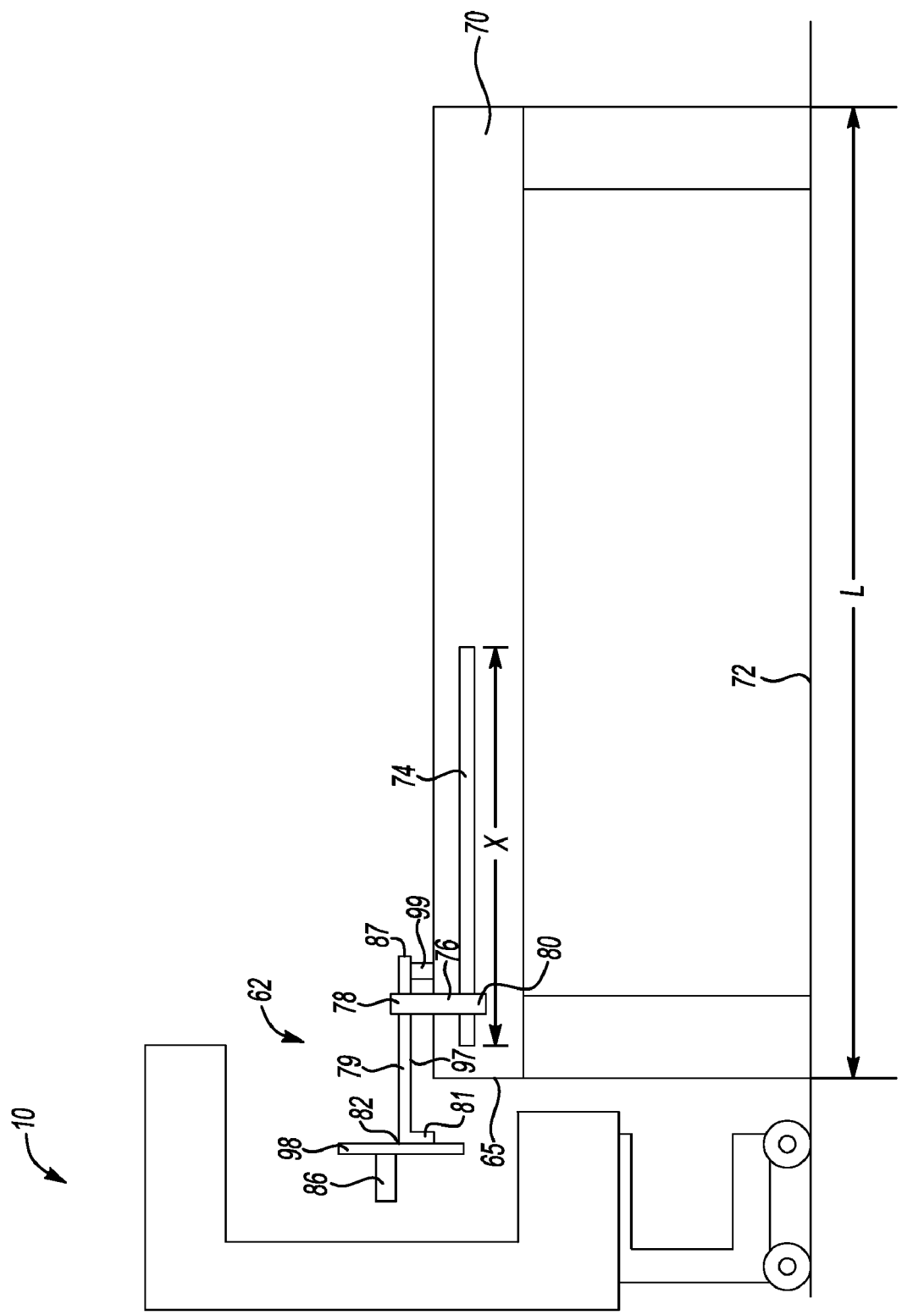
FIG. 4 illustrates a side view of a table with a head holder attached to the table.

As shown in FIG. 4, the head holder 62 is attached near an end 65 of the table 70 which is positioned on a floor 72. A bar 74 having a length x runs partially along a length L of the table 70. The bar 74 is commonly found on tables 70 used in hospitals. A bar 74 is located on each side of the table 70.

The head holder 62 is attached to each of the bars 74 with a clamp 76. There is one clamp 76 on each side of the table 70. In one example, the clamp 76 is made of aluminum. A first part 78 of the clamp 76 is secured to the head holder 62, and a second part 80 of the clamp 76 is secured to the bar 74 attached to the table 70.

The first part 78 of the clamp 76 can be loosened relative to the head holder 62 to allow the head holder 62 to move in a horizontal direction relative to the table 70 to adjust a position of the head holder 62 relative to the table 70. That is, the head holder 62 can move in a direction that is generally parallel to the length L of the table 70. When the head holder 62 is in the desired position, the first part 78 of the clamp 76 is tightened to secure the clamp 76 to the head holder 62.

The second part 80 of the clamp 76 can be loosened relative to the head holder 62 to allow the clamp 76 to move in a horizontal direction to adjust a position of the clamp 76 (and therefore the head holder 62) relative to the table 70. When the clamp 76 is in the desired position, the second part 80 of the clamp 76 is tightened to secure the clamp 76 to the bar 74.

Although a clamp 76 is described, it is to be understood that the head holder 62 can be attached to the table 70 in any manner possible. For example, the head holder 62 can be attached to the table 70 with Velcro straps.

Figure 5:
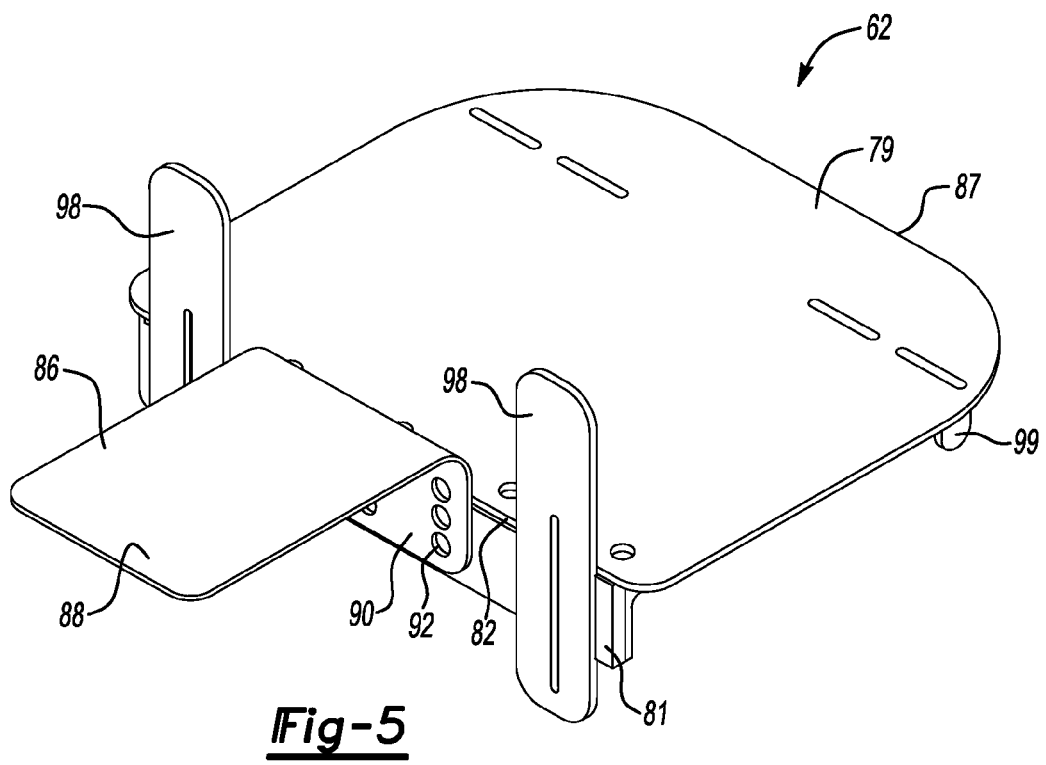
FIG. 5 illustrates a perspective view of the head holder.
Figure 6:
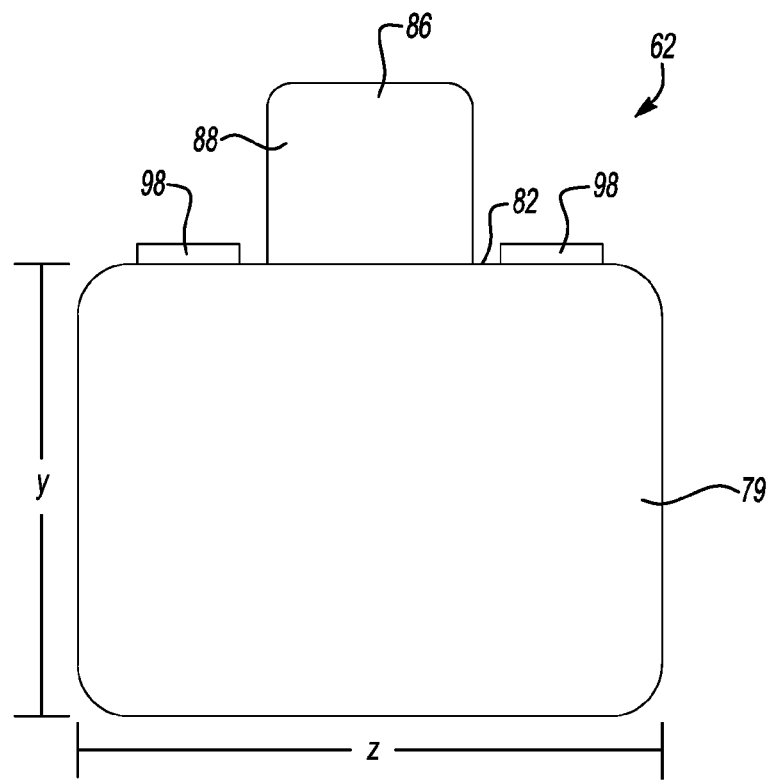
FIG. 6 illustrates a top view of the head holder.

FIGS. 5 and 6 illustrate a perspective view and a top view, respectively, of the head holder 62 of the present invention. The head holder 62 is made of carbon fiber and is radiolucent. The head holder 62 includes a base portion 79 on which the patient's P upper back and shoulders S rest. The base portion 79 is substantially planar and has a length z and a width y. In one example, the length z is approximately 19 inches, and the width y is approximately 20 inches.

Figure 7:
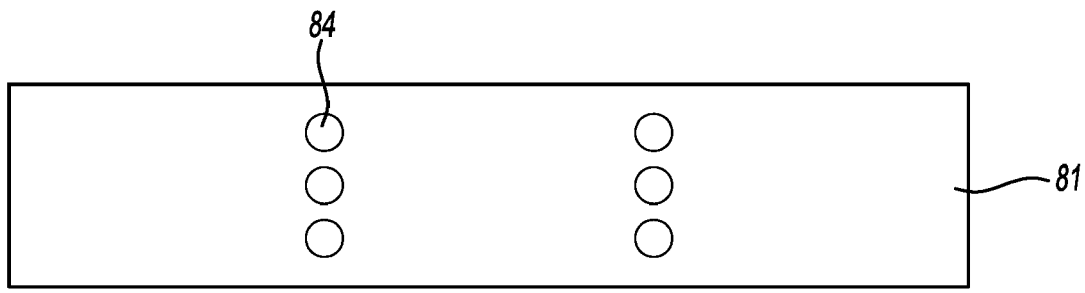
FIG. 7 illustrates a front view of a flange of a base portion of the head holder.

A flange 81 extends downwardly from an edge 82 of the base portion 79. The flange 81 includes a plurality of holes 84 (as shown in FIG. 7) which are used to attach a head rest 86, as described below. The first part 78 of the clamp 76 is clamped to the base portion 79. A downwardly extending leg 99 projects from a bottom side 97 of the base portion 79 near an edge 87 (which is opposite to the edge 82). The downwardly extending leg 99 rests on the table 70.

Figure 8:
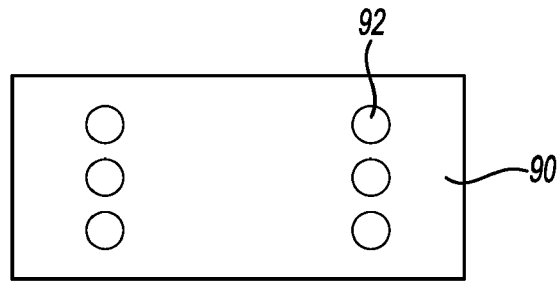
FIG. 8 illustrates a front view of a flange of a head rest of the head holder.
Figure 9:
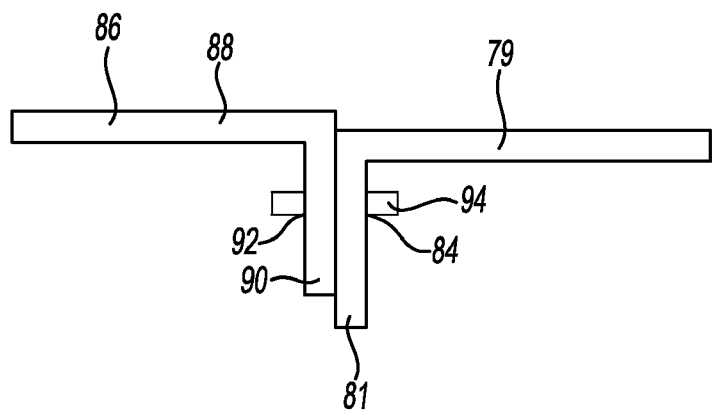
FIG. 9 illustrates the base portion and the head rest of the head holder attached by an attachment member.

The head holder 62 also includes the head rest 86. The head rest 86 includes a head retaining portion 88 and a flange 90 that extends downwardly from the head retaining portion 88. The head retaining portion 88 is substantially parallel to the base portion 79. The flange 90 includes a plurality of holes 92, as shown in FIG. 8. As shown in FIG. 9, at least one of the plurality of holes 84 of the flange 81 of the base portion 79 is aligned with at least one of the plurality of holes 92 of the flange 90 of the head retaining portion 88 to receive an attachment member 94 that secures the head retaining portion 88 to the base portion 79. The attachment member 94 can be removed and different holes 92 and 84 of the head rest 86 and the base portion 79, respectively, can be aligned to adjust the position of the head rest 86 in a generally vertical direction relative to the base portion 79.

The head holder 62 also includes two shoulder guards 98. One shoulder guard 98 is positioned on each side of the head retaining portion 88. As shown in FIG. 5, each shoulder guard 98 is substantially perpendicular to the base portion 79.

During a CT scan, the head holder 62 attached to the table 70 is received in the space 48 in the CT scanner 10. The leg 99 rests on the table 70. The radiolucent material of the head holder 62 received in the space 48 does not affect the quality of the resulting CT scan.

Figure 10:
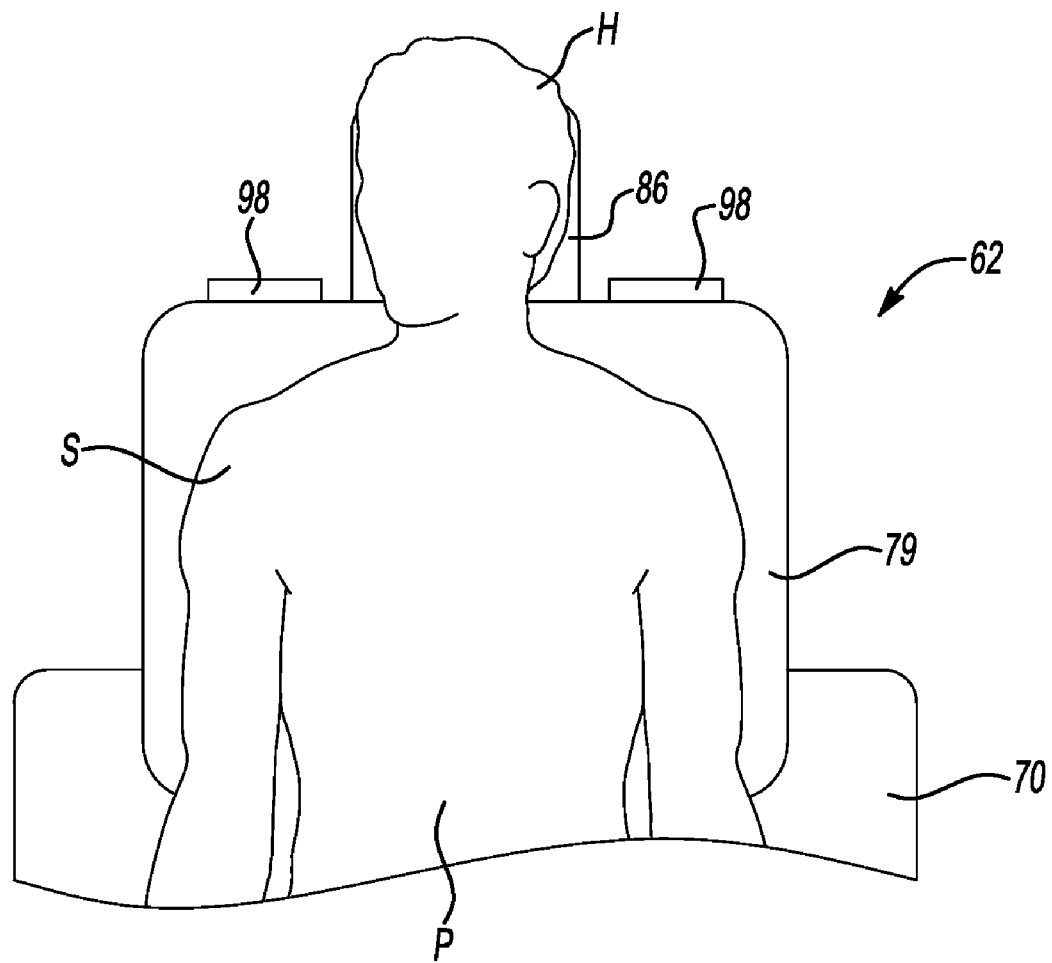
FIG. 10 illustrates a top view of the patient positioned on the table with the head holder.

FIG. 10 illustrates the patient P positioned on the head holder 62. A portion of the head H of the patient P is positioned on the head rest 86, and the upper back and shoulders S of the patient P are positioned on the base portion 79. The shoulders guards 98 retain the shoulders S to prevent the patient P from sliding relative to the table 70. The position of the head holder 62 can be moved in a horizontal direction and generally parallel to a length of the table 70 to customize the best position of the head holder 62 for each specific patient P. The head rest 86 can also be moved in a generally vertical direction relative to the base portion 79 to customize the best position of the head rest 86 relative to the base portion 79. When the patient P is positioned in the CT scanner 10 as shown in FIG. 4, the radiolucent head holder 62 is received in the space 48, minimizing the amount of metal table T in the space 48.

The foregoing description is only exemplary of the principles of the invention. Many modifications and variations are possible in light of the above teachings. It is, therefore, to be understood that within the scope of the appended claims, the invention may be practiced otherwise than using the example embodiments which have been specifically described. For that reason the following claims should be studied to determine the true scope and content of this invention.

What is claimed is:

1. A head holder attachable to a table, the head holder comprising:
  a head retaining portion to support a head of a patient, wherein a position of the head holder is adjustable relative to a table in a direction that is generally parallel to a length of the table, and the head retaining portion is substantially flat and defines a first plane; and
  a base portion to support and contact an upper back of the patient and defining a second plane, wherein the base portion is configured to support and contact the upper back of the patient when the head retaining portion is supporting the head of the patient,
  wherein the first plane defined by the head holder is located above the second plane defined by the base portion when the head holder is attached to the table.

2. The head holder as recited in claim 1 wherein at least a portion of the head holder is made of a radiolucent material.

3. A head holder attachable to a table, the head holder comprising:
  a head retaining portion to support a head of a patient, wherein a position of the head holder is adjustable relative to a table in a direction that is generally parallel to a length of the table;
  a base portion to support and contact an upper back of the patient, wherein the base portion is configured to support and contact the upper back of the patient when the head retaining portion is supporting the head of the patient; and
  a bar located on one side of the table and another bar located on another side of the table, and a clamp attaches one side of the base portion to the bar and another clamp attaches another side of the base portion to the another bar.

4. The head holder as recited in claim 3
  wherein each of the clamp and the another clamp includes a first part and a second part attached to the head holder and one of the bar and the another bar, respectively,
  wherein the first part and the second part can be loosened to allow the head holder to move in the direction to adjust the position of the head holder relative to the table, and
  wherein the first part and the second part are tightened to secure the head holder relative to the table.

5. A head holder attachable to a table, the head holder comprising:
  a head retaining portion to support a head of a patient, wherein a position of the head holder is adjustable relative to a table in a direction that is generally parallel to a length of the table;
  a base portion to support and contact an upper back of the patient, wherein the base portion is configured to support and contact the upper back of the patient when the head retaining portion is supporting the head of the patient; and
  a downwardly extending leg projecting from a bottom side of the base portion to rest on the table.

6. The head holder as recited in claim 1
wherein the base portion includes a base portion flange including a plurality of holes that extends downwardly from an edge of the base portion and the head retaining portion includes a head rest flange including a plurality of holes that extends downwardly from an edge of the head retaining portion,
wherein the plurality of holes of the head rest flange are vertically aligned and the plurality of holes of the base portion flange are vertically aligned, and
wherein a position of the head retaining portion relative to the base portion is vertically adjustable by aligning one of the plurality of holes of the head rest flange with one of the plurality of holes of the base portion flange, and an attachment member is received in the aligned holes to secure the head retaining portion to the base portion.

7. The head holder as recited in claim 6 wherein the base portion flange and the head rest flange are substantially planar.

8. A head holder attachable to a table, the head holder comprising:
a head retaining portion to support a head of a patient, wherein a position of the head holder is adjustable relative to a table in a direction that is generally parallel to a length of the table; and
a base portion to support and contact an upper back of the patient, wherein the base portion is configured to support and contact the upper back of the patient when the head retaining portion is supporting the head of the patient, wherein the head holder is received in a space between two arm sections of a gantry of a CT scanner, one arm section includes an x-ray source and the other arm section includes an x-ray detector that takes a plurality of x-ray images of the patient, and the gantry is rotatable about an axis.

9. The head holder as recited in claim 1 wherein the base portion is substantially planar and substantially parallel to the head retaining portion.

10. A head holder attachable to a table, the head holder comprising:
a head retaining portion to support a head of a patient, wherein a position of the head holder is adjustable relative to a table in a direction that is generally parallel to a length of the table;
a base portion to support and contact an upper back of the patient, wherein the base portion is configured to support and contact the upper back of the patient when the head retaining portion is supporting the head of the patient; and
shoulder guards that are substantially perpendicular to and attached to the base portion.

11. A head holder attachable to a table, the head holder comprising:
a head retaining portion to support a head of a patient, wherein a position of the head retaining portion relative to a base portion is adjustable in a generally vertical direction, and the head retaining portion is substantially flat and defines a first plane; and
the base portion to support and contact an upper back of the patient and defining a second plane, wherein the base portion is configured to support and contact the upper back of the patient when the head retaining portion is supporting the head of the patient,
wherein the first plane defined by the head holder is located above the second plane defined by the base portion when the head holder is attached to the table.

12. A head holder attachable to a table, the head holder comprising:
a head retaining portion to support a head of a patient, wherein a position of the head retaining portion relative to a base portion is adjustable in a generally vertical direction;
the base portion to support and contact an upper back of the patient, wherein the base portion is configured to support and contact the upper back of the patient when the head retaining portion is supporting the head of the patient; and
a bar located on one side of the table and another bar located on another side of the table, and a clamp attaches one side of the base portion to the bar, and another clamp attaches another side of the base portion to the another bar.

13. The head holder as recited in claim 12
wherein each of the clamp and the another clamp includes a first part and a second part attached to the head holder and one of the bar and the another bar, respectively,
wherein the first part and the second part can be loosened to allow the head holder to move in the direction to adjust the position of the head holder relative to the table, and
wherein the first part and the second part are tightened to secure the head holder relative to the table.

14. A head holder attachable to a table, the head holder comprising:
a head retaining portion to support a head of a patient, wherein a position of the head retaining portion relative to a base portion is adjustable in a generally vertical direction;
the base portion to support and contact an upper back of the patient, wherein the base portion is configured to support and contact the upper back of the patient when the head retaining portion is supporting the head of the patient; and
a downwardly extending leg projecting from a bottom side of the base portion to rest on the table.

15. The head holder as recited in claim 11
wherein the base portion includes a base portion flange including a plurality of holes that extends downwardly from an edge of the base portion and the head retaining portion includes a head rest flange including a plurality of holes that extends downwardly from an edge of the head retaining portion,
wherein the plurality of holes of the head rest flange are vertically aligned and the plurality of holes of the base portion flange are vertically aligned, and
wherein the position of the head retaining portion relative to the base portion is vertically adjustable by aligning one of the plurality of holes of the head rest flange with one of the plurality of holes of the base portion flange, and an attachment member is received in the aligned holes to secure the head retaining portion to the base portion.

16. The head holder as recited in claim 15 wherein the base portion flange and the head rest flange are substantially planar.

17. The head holder as recited in claim 11
wherein the base portion includes a base portion flange including a plurality of holes that extends downwardly from an edge of the base portion and the head retaining portion includes a head rest flange including a plurality of holes that extends downwardly from an edge of the head retaining portion, wherein the plurality of holes of the head rest flange are vertically aligned and the plurality of holes of the base portion flange are vertically aligned, and wherein the position of the head retaining portion relative to the base portion is vertically adjustable by aligning one of the plurality of holes of the head rest flange with one of the plurality of holes of the base portion flange, and an attachment member is received in the aligned holes to secure the head retaining portion to the base portion, wherein the head holder is received in a space between two arm sections of a gantry of a CT scanner, one arm section includes an x-ray source and the other arm section includes an x-ray detector that takes a plurality of x-ray images of the patient, and the gantry is rotatable about an axis.

18. The head holder as recited in claim 11 wherein at least a portion of the head holder is made of a radiolucent material.

19. The head holder as recited in claim 11 wherein a position of the head holder is adjustable relative to a table in a direction that is generally parallel to a length of the table.

20. A head holder attachable to a table, the head holder comprising:
a head retaining portion to support a head of a patient, wherein a position of the head holder is adjustable relative to a table in a direction that is generally parallel to a length of the table.
a base portion to support and contact an upper back of the patient, wherein the base portion is configured to support and contact the upper back of the patient when the head retaining portion is supporting the head of the patient; and
shoulder guards that are substantially perpendicular to and attached to the base portion.

21. The head holder as recited in claim 11 wherein the base portion is substantially planar and substantially parallel to the head retaining portion.

22. A CT scanner assembly comprising:
a gantry including a first arm section and a second arm section, wherein the gantry is rotatable about an axis;
an x-ray source mounted to the first arm section;
an x-ray detector mounted to the second arm section, wherein the x-ray detector takes a plurality of x-ray images of a patient;
a table having a length to support the patient, wherein a bar is located on one side of the table and another bar is located on another side of the table; and
a head holder attached to the bar and the another bar with a clamp and another clamp, respectively, the head holder including a head retaining portion to support a head of the patient and a base portion to support and contact an upper back of the patient, wherein the base portion is configured to support and contact the upper back of the patient when the head retaining portion is supporting the head of the patient, wherein at least a portion of the head holder is made of a radiolucent material and a position of the head holder is adjustable relative to the table in a direction that is generally parallel to the length of the table.

23. The CT scanner assembly as recited in claim 22 wherein the base portion is substantially planar and substantially parallel to the head retaining portion.

24. The CT scanner assembly as recited in claim 22 wherein the radiolucent material is carbon fiber.

25. The CT scanner assembly as recited in claim 22 wherein each of the clamp and the another clamp includes a first part and a second part attached to the head holder and one of the bar and the another bar, respectively,
wherein the first part and the second part can be loosened to allow the head holder to move in the direction to adjust the position of the head holder relative to the table, and
wherein the first part and the second part are tightened to secure the head holder relative to the table.

26. The CT scanner assembly as recited in claim 18 wherein a downwardly extending leg projects from a bottom side of the base portion and rests on the table.

27. The CT scanner assembly as recited in claim 22
wherein the base portion includes a base portion flange including a plurality of holes that extends downwardly from an edge of the base portion and the head retaining portion includes a head rest flange including a plurality of holes that extends downwardly from an edge of the head retaining portion,
wherein the plurality of holes of the head rest flange are vertically aligned and the plurality of holes of the base portion flange are vertically aligned, and
wherein a position of the head retaining portion relative to the base portion is vertically adjustable by aligning one of the plurality of holes of the head rest flange with one of the plurality of holes of the base portion flange, and an attachment member is received in the aligned holes to secure the head retaining portion to the base portion.

28. The CT scanner assembly as recited in claim 27 wherein the base portion flange and the head rest flange are substantially planar.

29. The CT scanner assembly as recited in claim 22 further including shoulder guards that are substantially perpendicular to and attached to the base portion.

30. The CT scanner assembly as recited in claim 22 wherein the head retaining portion is substantially flat.

31. A method of supporting a patient, the method comprising the steps of:
adjusting a position of a head holder relative to a table in a direction that is generally parallel to a length of the table, the head holder including a head retaining portion and a base portion, and the head retaining portion is substantially flat and defines a first plane and the base portion defines a second plane;
attaching the head holder to the table such that the first plane defined by the head holder is located above the second plane defined by the base portion when the head holder is attached to a table; and
positioning the patient on the table and the head holder such that the head retaining portion supports a head of the patient and the base portion supports and contacts an upper back of the patient, wherein the base portion is configured to support and contact the upper back of the patient when the head retaining portion is supporting the head of the patient.

* * * * *